United States Patent [19]

Clegg et al.

[11] Patent Number: 5,663,465
[45] Date of Patent: Sep. 2, 1997

US005663465A

[54] BY-PRODUCT RECYCLING IN OXYCHLORINATION PROCESS

[75] Inventors: Ian Michael Clegg, Middlewich; Ray Hardman, Chester, both of United Kingdom

[73] Assignee: EVC Technology AG, Zug, Switzerland

[21] Appl. No.: 433,385

[22] PCT Filed: Sep. 7, 1994

[86] PCT No.: PCT/GB94/01945

§ 371 Date: Aug. 15, 1995

§ 102(e) Date: Aug. 15, 1995

[87] PCT Pub. No.: WO95/07252

PCT Pub. Date: Mar. 16, 1995

[30] Foreign Application Priority Data

Sep. 7, 1993 [GB] United Kingdom .................. 9318505

[51] Int. Cl.[6] ................................................. C07C 17/10
[52] U.S. Cl. ........................................... 570/224; 570/225
[58] Field of Search ................................. 570/224, 225

[56] References Cited

U.S. PATENT DOCUMENTS

| 3,879,481 | 4/1975 | Sze et al. | 267/656 R |
| 3,937,744 | 2/1976 | Riegel | 260/656 R |

FOREIGN PATENT DOCUMENTS

| 704463 | 2/1965 | Canada | 570/224 |
| 1355870 | 2/1964 | France . | |
| 996323 | 6/1965 | United Kingdom | 570/224 |
| 1256245 | 12/1971 | United Kingdom . | |
| WO95/07250 | 3/1995 | WIPO . | |
| WO95/07251 | 3/1995 | WIPO . | |

*Primary Examiner*—Alan Siegel
*Attorney, Agent, or Firm*—Woodcock Washburn Kurtz Mackiewicz & Norris LLP

[57] ABSTRACT

A method for the catalytic oxychlorination of ethane to VCM comprising the steps of combining ethane and a chlorine source in an oxychlorination reactor with a suitable catalyst to promote the oxychlorination of the ethane, collecting the resultant VCM and by-productsand recycling the by-products to the oxychlorination reactor to participate in the reaction therein.

5 Claims, 1 Drawing Sheet

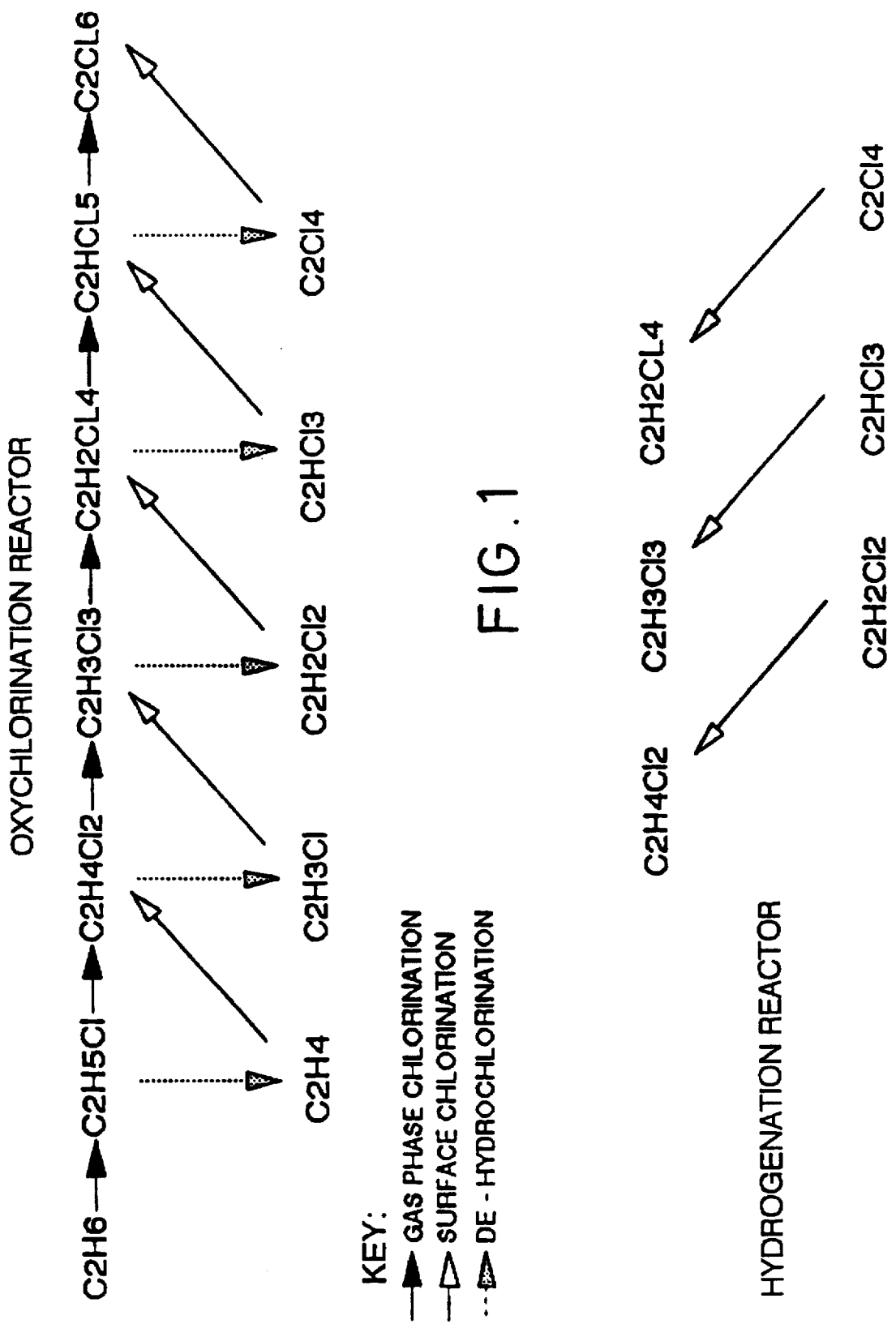

BY-PRODUCT RECYCLING IN OXYCHLORINATION PROCESS

The present invention relates to a method for improving the efficiency of the oxychlorination of ethane to vinyl chloride monomer (VCM). The increase in efficiency is obtained by recycling the by-products of the reaction.

Most commercial processes for the production of VCM utilise ethylene and chlorine as the raw materials. Ethylene is in general chlorinated by contact with chlorine and a catalyst in liquid 1,2-dichloroethane. The dichloroethane is subsequently dehydrochlorinated at an elevated temperature to yield VCM and hydrogen chloride.

The use of ethylene as a starting material is a significant factor in the cost of producing VCM. In general, significant reductions in this cost can only be achieved by economies of scale since established processes are operating at close to maximum efficiency.

A further disadvantage of the use of ethylene is that the dehydrochlorination of the 1,2-dichloroethane intermediate yields hydrogen chloride. Disposal thereof is usually achieved by catalytic oxychlorination with ethylene in a further processing step to yield more 1,2-dichloroethane.

An alternative, known method for the production of VCM involves the use of ethane. The use of alternative hydrocarbon raw materials, of which ethane is the primary candidate, immediately addresses the issue of the cost of ethylene by substituting it with a cheaper alternative. Additionally, the chemistry of VCM production using alternative hydrocarbons may hold advantages. For example, VCM production can be achieved in a single step.

Three chemical approaches are known for the conversion of ethane to VCM. These are gas phase chlorination, catalysed oxidation and oxychlorination. Of these, a process based on oxychlorination is the most attractive:

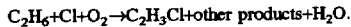

$$C_2H_6 + Cl + O_2 \rightarrow C_2H_3Cl + \text{other products} + H_2O.$$

The chlorine source may be $Cl_2$, HCl or a chlorinated hydrocarbon. Where HCl is the source, the opportunity arises to utilise one of the intermediate products of VCM production from ethylene.

The production of VCM from ethane has not enjoyed commercial success. A number of attempts have been made, but the processes used have suffered from a number of drawbacks which, while inconvenient in a laboratory, become unacceptable when the process is applied on an industrial scale.

In our copending U.K. Patent Application No. 9318501.5, filed contemporaneously herewith, we describe an oxychlorination catalyst and a set of reaction conditions which are suitable for the operation of an ethane oxychlorination process on an industrial scale. Furthermore, in our copending U.K. Patent Application No. 9318507.2, also filed contemporaneously herewith, we describe a method for increasing the selectivity of the oxychlorination reaction to VCM.

However, this selectivity can never be absolute. In our copending U.K. Patent Application No. 9318501.5, the generation of by-products is carefully assessed, and even under the most favourable conditions large amounts of chlorinated hydrocarbons other than VCM are produced.

A major attraction of the use of ethane for the production of VCM is the cost advantage of the raw material. In order for this cost advantage to be maintained, it is important to eliminate the sources of inefficiency in the reaction process. Therefore, there is a requirement for a method for recovering the by-products of the reaction. Since these by-products cannot be disposed of by direct sales, it would be advantageous to be able to derive a useful saleable product therefrom at the minimum cost.

In the prior art, the generation of chlorinated by-products of the oxychlorination reaction is largely ignored.

For example, in GB 1256245 (Princeton Chemical Research, Inc.) "other chlorinated materials" are produced at a level of about one tenth of the yield of vinyl chloride. There is no suggestion in GB 1256245 as to how such by-products should be dealt with. However, it can be seen that they constitute an appreciable fraction of the total yield of the reaction.

U.S. Pat. No. 3,879,481 (Lummus Co.) acknowledges the production of chlorinated by-products in the form of chlorinated hydrocarbons, such as trichloroethane, trichloroethylene, tetrachloroethane and the like. It is suggested that these by-products be burned, resulting in the loss of their feedstock value. Even if the hydrogen chloride produced is recovered, the carbon content of the by-products is lost.

The chlorinated by-products formed during the oxychlorination of ethane to VCM are conveniently categorised as saturates, unsaturates and combustion products.

Saturates include ethyl chloride, 1,1 dichloroethane, 1,2 dichloroethane and 1,1,2 trichloroethane. Combustion products include carbon tetrachloride, chloroform and dichloromethane. Unsaturates include 1,1 dichloroethylene, cis 1,2 dichloroethylene, trans 1,2 dichloroethylene, trichloroethylene and perchloroethylene.

According to a first aspect of the present invention, therefore, there is provided a method for the catalytic oxychlorination of ethane to VCM comprising the steps of:

a) combining ethane and a chlorine source in an oxychlorination reactor with a suitable catalyst to promote the oxychlorination of the ethane, and collecting the resultant VCM and by-products; and b) recycling the byproducts to the oxychlorination reactor to participate in the reaction therein.

It has been found that it is possible to recycle the chlorinated hydrocarbon by-products directly to the oxychlorination reactor.

While this achieves some partial success, the total conversion of by-products to VCM is low.

This is because the reactions which occur in the oxychlorination reaction are unable to convert unsaturated chlorinated hydrocarbons to VCM. Furthermore, many saturated chlorinated hydrocarbons will be converted to unsaturated chlorinated hydrocarbons by dehydrochlorination, and will therefore not be available for conversion to VCM.

Therefore, it is necessary to convert the chlorinated hydrocarbon by-products into a form from which VCM may eventually be generated, by means of a further process step.

Preferably, therefore, unsaturated hydrocarbons are converted to saturated species by a hydrogenation step.

Saturated chlorinated hydrocarbons may be converted by dehydrochlorination and, if necessary, additional hydrogenation reactions into unsaturated hydrocarbons and eventually into VCM. FIG. 1 shows the reactions which occur in the oxychlorination and hydrogenation reactors used in the present invention.

By recycling the unsaturated by-products through a hydrogenation step, all of the chlorinated hydrocarbon by-products of the oxychlorination reaction may be recovered and their feedstock value is not wasted.

In the hydrogenation step, a feed of chlorinated by-products is brought together with hydrogen over a catalyst bed at elevated temperature and pressure. Suitable catalysts include platinum, palladium and rhodium, preferably operated at between 20° and 250° C., advantageously between 50° and 150° C., in a trickle bed reactor. Preferably, a large excess of hydrogen is used. However, any suitable catalyst known in the art is envisaged for use in the process of the invention, under appropriate operating conditions.

The unsaturated chlorinated hydrocarbons are preferably byproducts of the oxychlorination of ethane. However, it is envisaged that they may be derived from other processes.

The unsaturated chlorinated hydrocarbons may be fed to the hydrogenation reactor in an essentially pure feed. However, in a preferred embodiment of the invention, they are supplied in an unpurified form together with saturated chlorinated hydrocarbon by-products and combustion products from the oxychlorination reactor. This eliminates the necessity for a separation stage to separate saturated from non-saturated by-products and combustion products.

The saturates are largely unaffected by this treatment, although under certain conditions they may undergo some hydro-dechlorination leading to the production of ethane. Combustion products will also undergo hydro-dechlorination, to yield methane and HCl.

Preferably, the components of the by-product feed will comprise these given below, within the mole fraction ratios given:

|  | MINIMUM | MAXIMUM |
|---|---|---|
| 1,1 dichloroethylene, | 0 | 10 |
| cis 1,3 dichloroethylene, | 0 | 10 |
| trans 1,3 dichloroethylene, | 0 | 20 |
| trichloroethylene, | 0 | 10 |
| perchloroethylene, | 0 | 10 |
| ethyl chloride, | 0 | 20 |
| 1,1 dichloroethane (EDC), | 0 | 10 |
| 1,2 dichloroethane, | 0 | 90 |
| 1,1,2 trichloroethane | 0 | 30 |
| carbon tetrachloride | 0 | 20 |
| chloroform | 0 | 20 |
| dichloromethane | 0 | 10 |
| sym-tetrachloroethane | 0 | 5 |

The reactor feed can also contain relatively small amounts of other materials such as chlorinated butanes, chlorinated butadienes and other chlorinated materials as well as hydrocarbons such as ethane and ethylene.

The invention may be put to use in conjunction with any oxychlorination system. However, the use of the catalyst and conditions described in our copending U.K. Patent Application No. 9318501.5 is preferred.

Additionally, the selectivity of the oxychlorination reaction may be improved by using an excess of HCl gas in the oxychlorination reactor, as described in our copending U.K. Patent Application No. 9318507.2. The use of such a process advantageously reduces the quantity of combustion products generated, thereby further improving the total efficiency of the process.

The invention will now be described, for the purposes of illustration only, by way of the following example.

FIG. 1 is a schematic representation of the reactions which take place in oxychlorination and hydrogenation reactors.

Into a fluidised bed reactor are fed the following components:

| Feeds |  |  |
|---|---|---|
| Ethane | 1.0 |  |
| Oxygen | 0.85 |  |
| Direct chlorination product |  |  |
| EDC | 0.35 | (0.35 chlorine feed) |
| Carbon oxides | 1.1 |  |
| Hydrogenation recycle |  |  |
| Ethyl chloride | 0.37 |  |
| EDC | 0.78 |  |
| 1,1 dichloroethane | 0.02 |  |
| 1,1,2-trichloroethane | 0.04 |  |
| Sym-tetrachloroethane | 0.01 |  |
| Carbon tetrachloride | 0.03 |  |
| Hydrogen chloride recycle |  |  |
| HCl | 0.1 |  |

The above molar proportions represent the steady state operating flows into the reactor for the process. Chlorine enters the process as elemental chlorine fed to the direct chlorination reactor.

Ethane is mixed with the HCl recycle and fed to the reactor below the catalyst support plate. In the windbox it mixes with the vaporised hydrogenation recycle and the direct chlorination products. The combined streams are at a temperature of 150° C. and a pressure of 5.5 bara.

The mixture passes through the support grid to fluidise the catalyst which operates at a temperature of 450° C. The oxygen feed is added via a gas sparger which is situated just above the support grid. The residence time is 12 seconds and the reaction temperature is maintained steady by removing reaction heat by heat transfer coils immersed in the bed and cooled by circulating hot salt. The product spectrum, on the same basis as the feed given above, is:

| Products |  |
|---|---|
| Ethane | 0.24 |
| Ethylene | 0.35 |
| VCM | 0.70 |
| Oxygen | 0.08 |
| EDC | 0.35 |
| Carbon oxides | 1.24 |
| Ethyl chloride | 0.37 |
| EDC | 0.78 |
| Dichloroethylenes | 0.05 |
| Trichloroethylene | 0.01 |
| 1,1,2-trichloroethane | 0.02 |
| Perchloroethylene | 0.01 |
| Carbon tetrachloride | 0.03 |
| HCl | 0.1 |
| Water | 1.31 |

We have found that as the HCl content of the gases coming out of the ethane oxychlorination reactor is allowed to fall to a very low level (almost complete reaction) then the amount of ethane which is converted to burning products rises steeply. By maintaining an excess of HCl the burning can be reduced from 20% (no HCl in the off gases) to 3% (10% HCl in the off gas). We have also found that it is possible to reduce the operating temperature of the reactor to 450° C., whilst still maintaining acceptable feed conversion and selectivity, by increasing the residence time of the reactants from 2 seconds to 12 seconds. This feature is important because known fabrication metals suffer greatly enhanced corrosion/erosion above 470° C.

The reaction mixture, given above, is separated into a water stream, an anhydrous HCl stream, a dry lights stream (all components lighter than VCM), a pure VCM stream and a heavy by-products stream.

Water is removed from the reactor products by first performing a partial condensation which gives an aqueous HCl phase, a wet liquid organic phase and a wet vapour phase. The aqueous phase is mixed with a calcium chloride solution and then distilled to produce a top product of anhydrous HCl which is recycled to the reactor. The base product is taken off as a side stream vapour which is condensed to give an uncontaminated water stream. The calcium chloride stream is recycled to the column feed. The wet liquid phase is azeotropically dried in a distillation column. The wet top product is recycled back to the phase separation section whilst the dry base product is pumped forward for distillative separation. The wet vapour is dried by contacting it countercurrently with 20% w/w HCl solution cooled to −20° C. A purge is taken from this stream to the calcium chloride column in order to preserve the materials balance. The dry vapour is then compressed and transferred to the distillation section.

Compressed vapour products and the dried liquid organic stream are fed together to a distillation column (lights column) which operates with ethane as the light key and VCM as the heavy key. After heat interchange with the column feed the vapour product is reacted with chlorine to produce EDC from the ethylene component of the feed. This can be done in a vapour phase fluid bed, a fixed bed or in a conventional liquid phase reactor.

A fluidised bed vapour phase direct chlorinator is preferred for this reaction as the heat of reaction can be recovered as steam and there is no product contamination, due to iron for example, to impact on the environment. The reactor operates at 6 bara and 200° C. The off gas is recycled to the oxychlorination reactor but a small purge is taken from the stream to keep the carbon oxides in balance. EDC is removed from the purge stream using carbon bed adsorption. The lean gas is incinerated.

The base flow from the lights column is distilled (VCM column) to remove VCM as top product. The base product is reacted with hydrogen in a trickle bed reactor. In this reactor any olefinic species (e.g. dichloroethylenes, trichloroethylene and perchloroethylene) are converted to their saturated counterparts. The reaction takes place adiabatically at 10 bara and 75° C. with a tenfold hydrogen excess. The saturated stream is then vaporised and recycled to the oxychlorination reactor where the saturates dehydrochlorinate. By this mechanism all compounds, other than carbon tetrachloride, eventually convert to VCM.

We claim:

1. A method for the catalytic oxychlorination of ethane to VCM comprising the steps of:
   (a) combining ethane and a chlorine source in an oxychlorination reactor with a suitable catalyst to promote the oxychlorination of the ethane, and collecting the resultant VCM and byproducts;
   (b) recycling unconverted feeds and saturated byproducts to the oxychlorination reactor to participate in the reaction therein;
   (c) treating unsaturated chlorinated hydrocarbon byproducts in a hydrogenation step to convert them to their saturated chlorinated hydrocarbon counterparts and passing said saturated chlorinated hydrocarbon counterparts to the oxychlorination reactor to participate in the reaction therein; and
   (d) treating ethylene byproduct in a chlorination step to convert it to dichloroethane and passing said dichloroethane to the oxychlorination reactor to participate in the reaction therein.

2. The method of claim 1 wherein the unsaturated chlorinated hydrocarbons are hydrogenated in step (c) by reaction with a molar excess of hydrogen over a catalyst bed.

3. The method of claim 2, wherein a rhodium, palladium or platinum catalyst is used in step (c).

4. The method of claim 2 or claim 3, wherein the reaction temperature in the hydrogenation step (c) is between 50° and 150° C.

5. The method of claim 1, wherein in step (c) said unsaturated chlorinated hydrocarbons are fed to the hydrogenation reactor together with saturated chlorinated hydrocarbon and combustion byproducts of the oxychlorination reaction.

* * * * *